US008155894B2

(12) United States Patent  
Kabumoto

(10) Patent No.: US 8,155,894 B2  
(45) Date of Patent: Apr. 10, 2012

(54) X-RAY INSPECTION APPARATUS

(75) Inventor: Takashi Kabumoto, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 329 days.

(21) Appl. No.: 12/548,496

(22) Filed: Aug. 27, 2009

(65) Prior Publication Data

US 2010/0057380 A1     Mar. 4, 2010

(30) Foreign Application Priority Data

Aug. 28, 2008   (JP) ................................ 2008-220434

(51) Int. Cl.
*G01B 15/00* (2006.01)
*G06F 19/00* (2011.01)

(52) U.S. Cl. ........................................................ 702/40

(58) Field of Classification Search ...................... 702/40
See application file for complete search history.

(56) References Cited

U.S. PATENT DOCUMENTS

| | | | |
|---|---|---|---|
| 3,789,226 A * | 1/1974 | Green et al. | 378/61 |
| 3,958,078 A * | 5/1976 | Fowler et al. | 348/127 |
| 6,049,585 A * | 4/2000 | Ocleppo | 378/57 |
| 6,777,676 B1 * | 8/2004 | Wang et al. | 850/8 |
| 7,027,070 B2 * | 4/2006 | Makinen | 345/619 |
| 7,202,475 B1 * | 4/2007 | Testoni | 250/310 |
| 7,522,700 B2 * | 4/2009 | Bavendiek et al. | 378/58 |

FOREIGN PATENT DOCUMENTS

JP         2002-98653 A      4/2002

* cited by examiner

*Primary Examiner* — Cindy H Khuu  
(74) *Attorney, Agent, or Firm* — Global IP Counselors, LLP

(57) ABSTRACT

An X-ray inspection apparatus includes a storage device, a setting device, a determining device, a calculating device and a display control device. The setting device is configured to set a hypothetical reference value that is different from an actual reference value that was used during the inspection of the articles. The determining device is configured to determine whether a contaminant exists inside each of the articles based on a result of a comparison between the hypothetical reference value and each of detection data stored in the storage device. The calculating device is configured to calculate a hypothetical contaminant existence rate as a ratio of a number of the articles in which the determining device has determined that a contaminant exists with respect to a total number of the articles. The display control device is configured to control a display section to indicate the hypothetical contaminant existence rate.

8 Claims, 12 Drawing Sheets

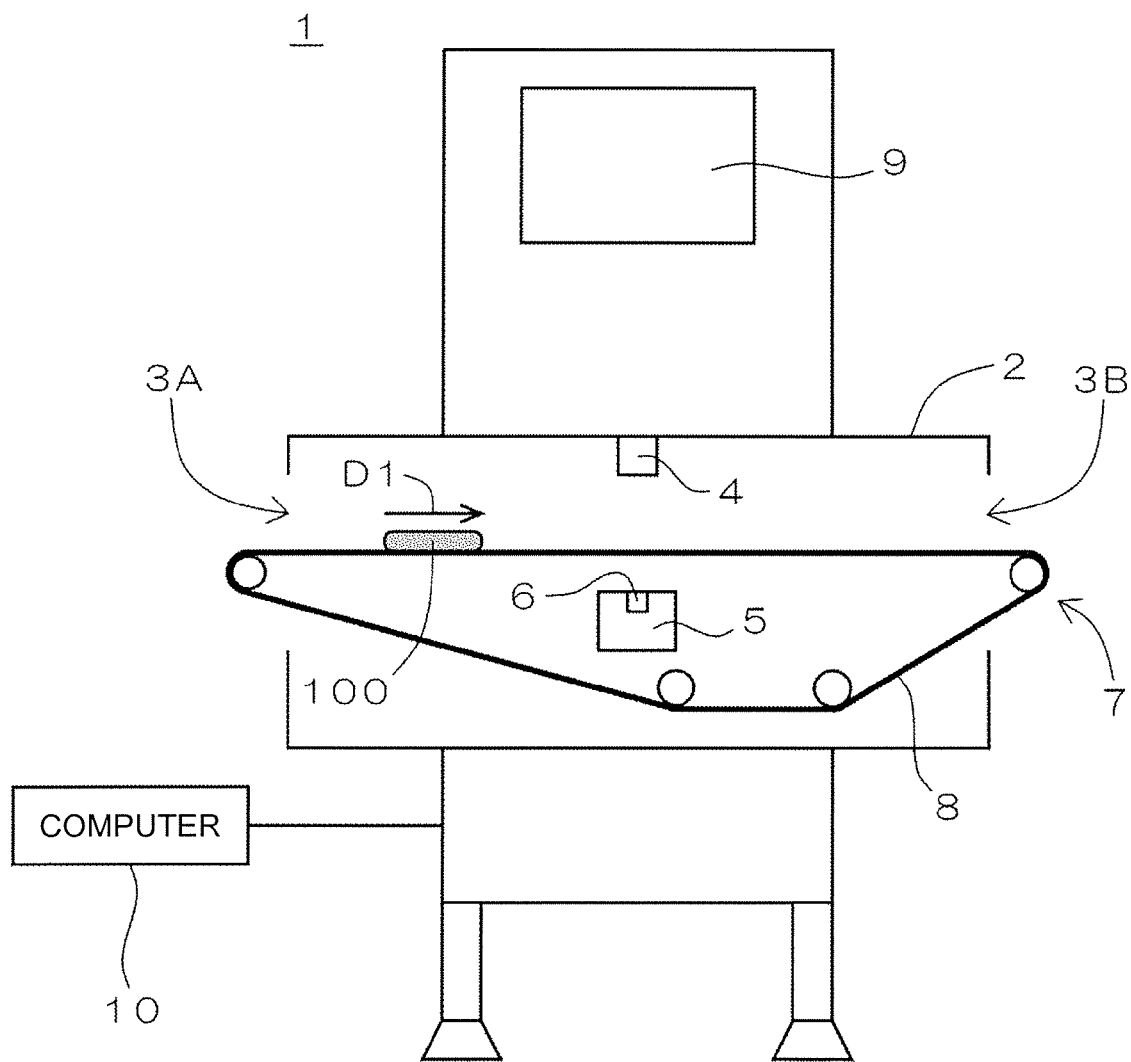
F I G. 2

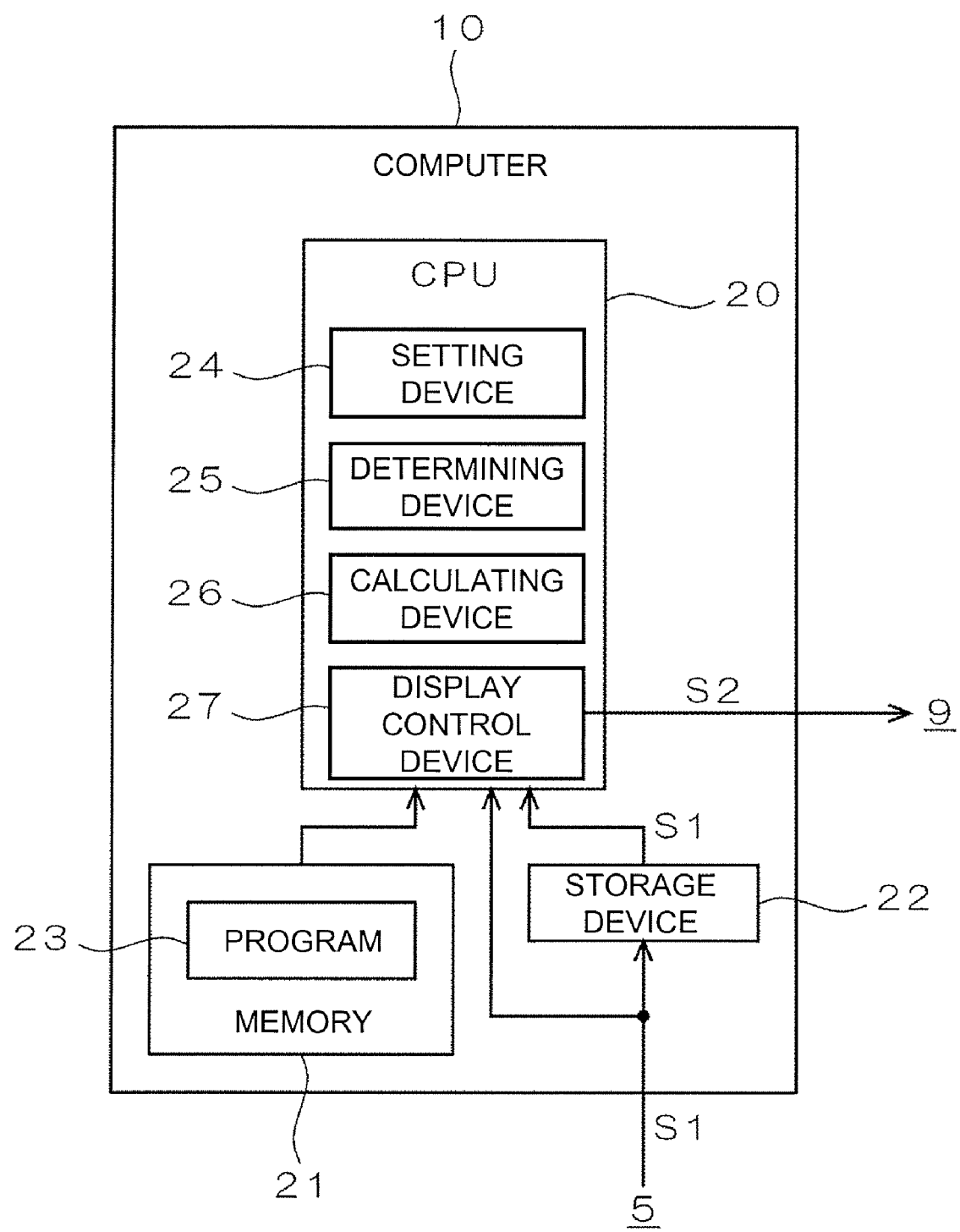
F I G. 3

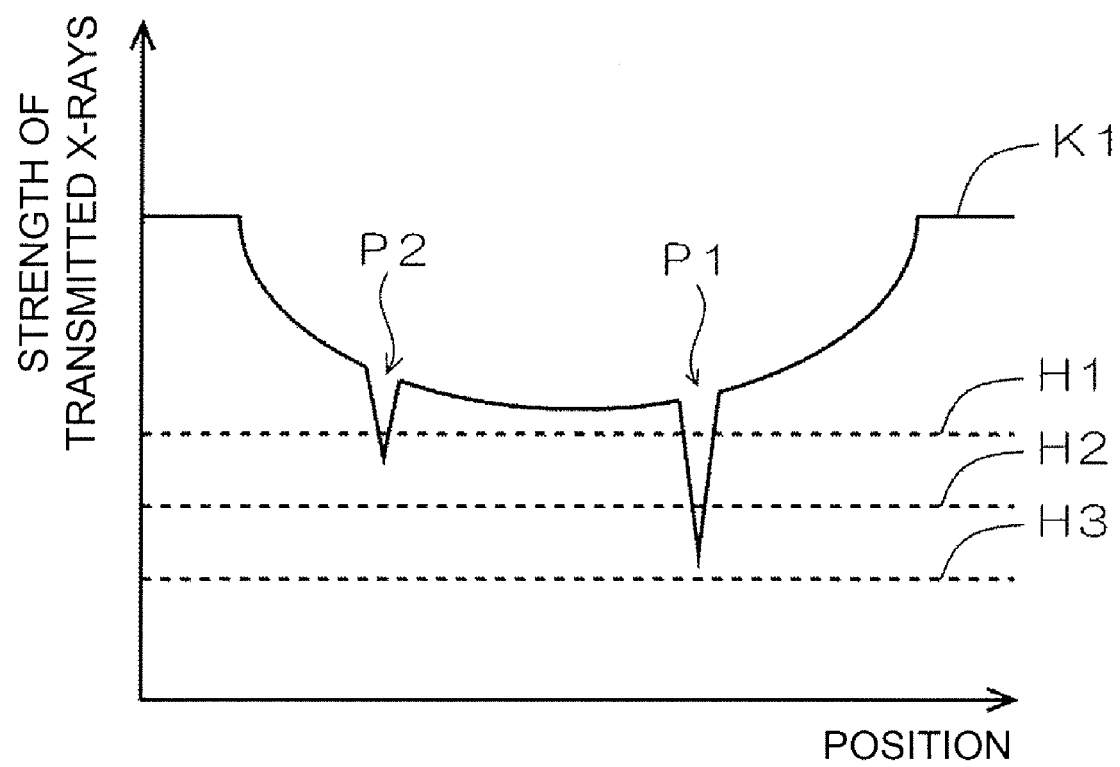
F I G. 4

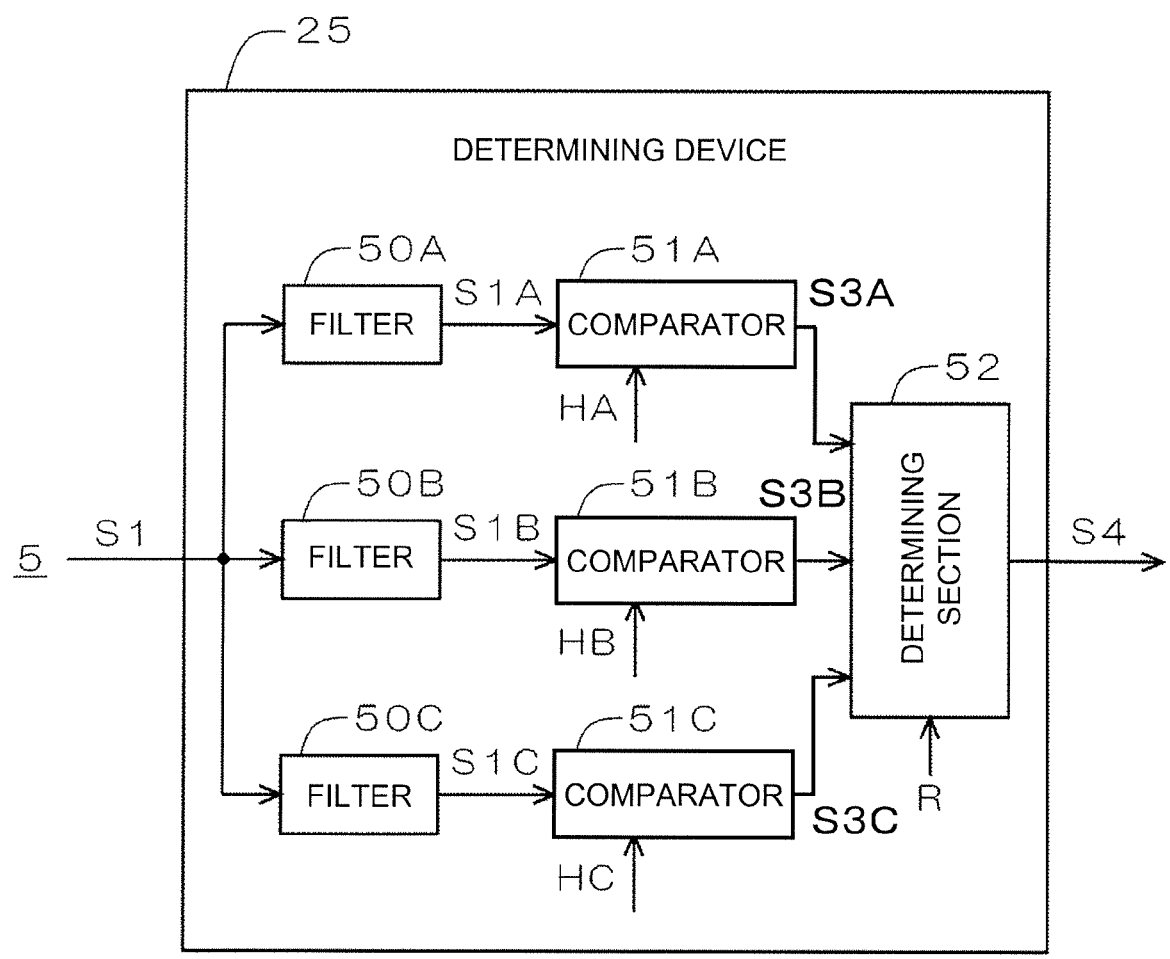
F I G. 8

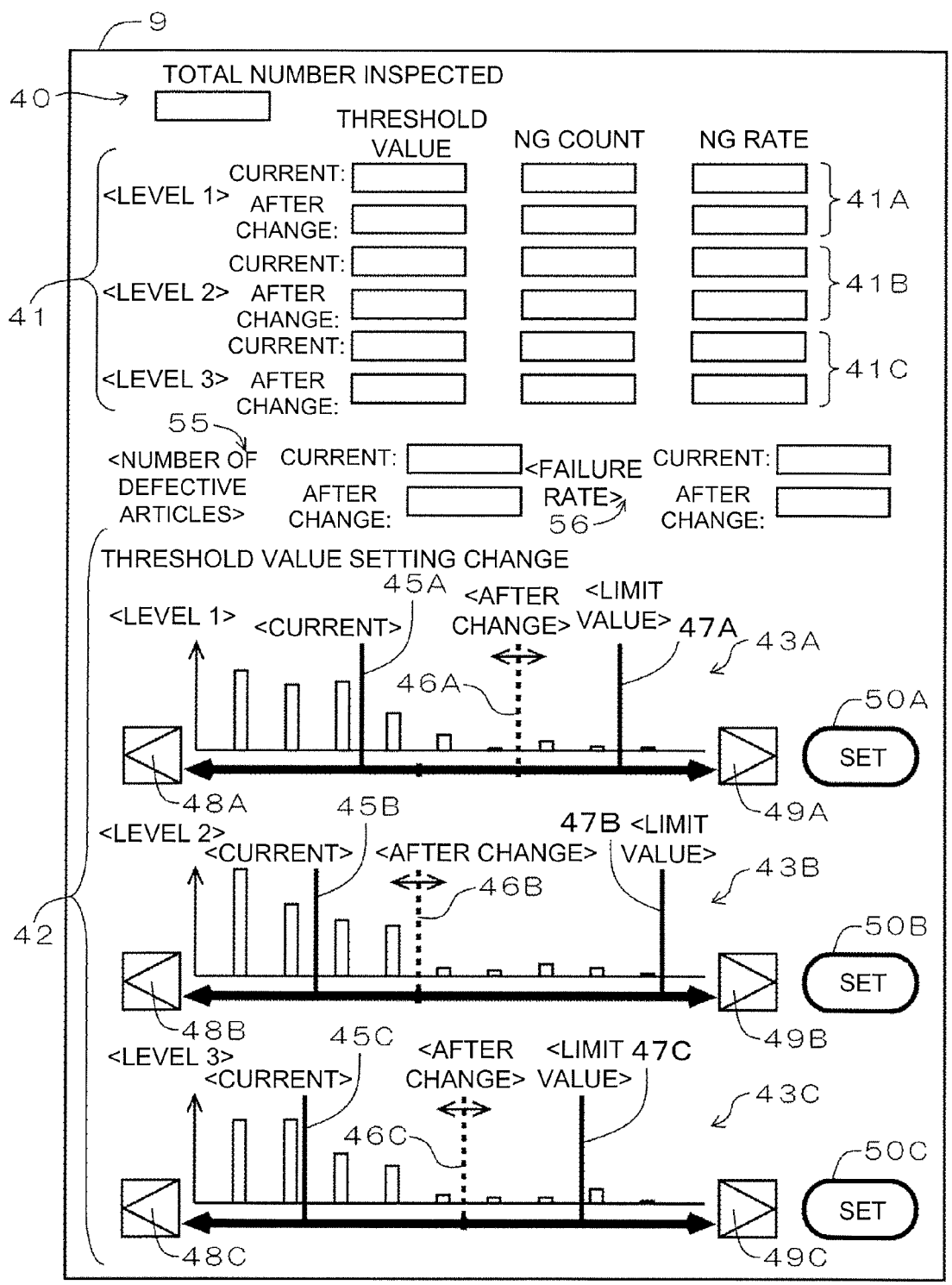
F I G. 9

X-RAY INSPECTION APPARATUS

CROSS-REFERENCE TO RELATED APPLICATIONS

This application claims priority to Japanese Patent Application No. 2008-220434 filed on Aug. 28, 2008. The entire disclosure of Japanese Patent Application No. 2008-220434 is hereby incorporated herein by reference.

BACKGROUND

1. Technical Field

The present invention relates to an X-ray inspection apparatus.

2. Related Art

In an X-ray inspection apparatus, an X-ray beam is emitted at an article from an X-ray source and an X-ray that has passed through the article (transmitted X-ray) is detected with an X-ray sensor. A strength of the transmitted X-ray detected by the X-ray sensor is then compared to a prescribed threshold value that is set in advance and a determination is made as to whether the article is defective or not based on the result of the comparison (e.g., Japanese Laid-Open Patent Publication No. 2002-98653). If a contaminant exists inside an article, the strength of a transmitted X-ray will decrease greatly at the location where the contaminant exists. Consequently, an article can be determined to be defective (contaminated) when the strength of transmitted X-ray is below a prescribed threshold value.

SUMMARY

As described above, in the X-ray inspection apparatus, an article is determined to be defective or not based on the result of a comparison between a strength of an transmitted X-ray and a threshold value. Therefore, in order to accomplish an appropriate inspection, it is necessary to set the threshold value to an appropriate level. If the level of the threshold value is set too low, then an article in which contamination exists will be determined to be non-defective. Conversely, if the level of the threshold value is set too high, then signal noise or the like will be detected as contamination and an article in which a contaminant does not exist will be determined to be defective, thereby causing a failure rate (ratio of defective articles to the total number of articles inspected) to increase.

In order to maintain a constant inspection standard, once a manufacturing line of the article started to be operated, the threshold value setting cannot be changed while the manufacturing line of the article is running. Therefore, if the set reference value becomes inappropriate, e.g., if the level of the threshold value is set too low and the failure rate becomes extremely high, then the manufacturing line needs to be temporarily stopped in order to change the threshold value setting. Consequently, the utilization rate of the manufacturing line declines. Additionally, even if a line worker changes the threshold value setting in accordance with a feeling (mental estimation) and experience alone, there is the possibility that the changed threshold value will still be inappropriate and the manufacturing line will have to be stopped again, thus further decreasing the utilization rate.

The present invention was conceived in view of these issues and its object is to provide an X-ray inspection apparatus that provides a line worker with an index for changing the setting of the reference value (threshold value) and thereby enables the reference value setting to be changed more efficiently.

An X-ray inspection apparatus according to the first aspect is an X-ray inspection apparatus configured to emit an X-ray beam at an article from an X-ray emitting section, detect an X-ray that has passed through the article with an X-ray detecting section, and determine whether the article is defective or not based on a result of a comparison between a strength of the X-ray detected by the X-ray detecting section and a prescribed reference value. The X-ray inspection apparatus includes a storage device, a setting device, a determining device, a calculating device, and a display control device. The storage device is configured to store a plurality of detection data related to strengths of the X-rays. The plurality of detection data are acquired by the X-ray detecting section during inspection of a plurality of articles. The setting device is configured to set a hypothetical reference value that is different from an actual reference value that was used during the inspections of the articles. The determining device is configured to determine if a contaminant exists inside each of the articles based on a result of a comparison between the hypothetical reference value and each of the detection data stored in the storage device. The calculating device is configured to calculate a hypothetical contaminant existence rate as a ratio of a number of articles in which the determining device has determined that a contaminant exists with respect to a total number of articles. The display control device is configured to control a display section to indicate the hypothetical contaminant existence rate.

Therefore, when it becomes necessary to change an actual reference value setting, a worker sets a hypothetical reference value as desired by using the setting device, and a hypothetical contaminant existence rate corresponding to the hypothetical reference value is thereby displayed on the display section. As a result, the worker can use the hypothetical contaminant existence rate indicated on the display section as an index so as to set the actual reference value more efficiently. Additionally, the hypothetical contaminant existence rate is not a prediction based on a simulation or the like but, instead, is calculated based on detection data acquired during the actual inspection of a plurality of articles. Consequently, an accurate hypothetical contaminant existence rate can be provided to a worker.

According to another aspect of the present invention, a computer readable medium is embedded with a program executed by a computer that controls an X-ray inspection apparatus to emit an X-ray beam at an article from an X-ray emitting section, to detect an X-ray that has passed through the article with an X-ray detecting section, and to determine whether the article is defective based on a result of a comparison between a strength of the X-ray detected by the X-ray detecting section and a prescribed reference value. The program includes instructions to: retrieve a plurality of detection data related to strengths of the X-rays acquired by the X-ray detecting section during inspection of a plurality of articles; to set a hypothetical reference value as the prescribed reference value, the hypothetical reference value being different from an actual reference value that was used during the inspection of the articles; to determine whether a contaminant exists inside each of the articles based on a result of a comparison between the hypothetical reference value and each of the detection data stored in the storage device; to calculate a hypothetical contaminant existence rate as a ratio of a number of the articles in which the determining device has determined that a contaminant exists with respect to a total number of the articles; and to control a display section to indicate the hypothetical contaminant existence rate.

Therefore, when it becomes necessary to change an actual reference value setting, a worker sets a hypothetical reference value as desired by using the setting device and a hypothetical contaminant existence rate corresponding to the hypothetical reference value is thereby displayed on the display section. As a result, the worker can use the hypothetical contaminant existence rate indicated on the display section as an index so as to set the actual reference value more efficiently. Additionally, the hypothetical contaminant existence rate is not a prediction based on a simulation or the like but, instead, is calculated based on detection data acquired during the actual inspection of a plurality of articles. Consequently, an accurate hypothetical contaminant existence rate can be provided to a worker.

BRIEF DESCRIPTION OF THE DRAWINGS

Referring now to the attached drawings which form a part of this original disclosure:

FIG. 2 is a schematic frontal view showing another example configuration of the X-ray inspection apparatus according to the embodiment of the present invention.

FIG. 3 is a block diagram illustrating constituent features of a computer operatively coupled to the X-ray inspection apparatus according to the embodiment of the present invention.

FIG. 4 shows an example of setting the threshold value.

FIG. 8 is a block diagram showing a configuration of a determining section according to a first modified example.

FIG. 9 shows an example of an image displayed on the display section during a threshold value change operation according to the first modified example.

DETAILED DESCRIPTION OF EXEMPLARY EMBODIMENTS

Figure 1:
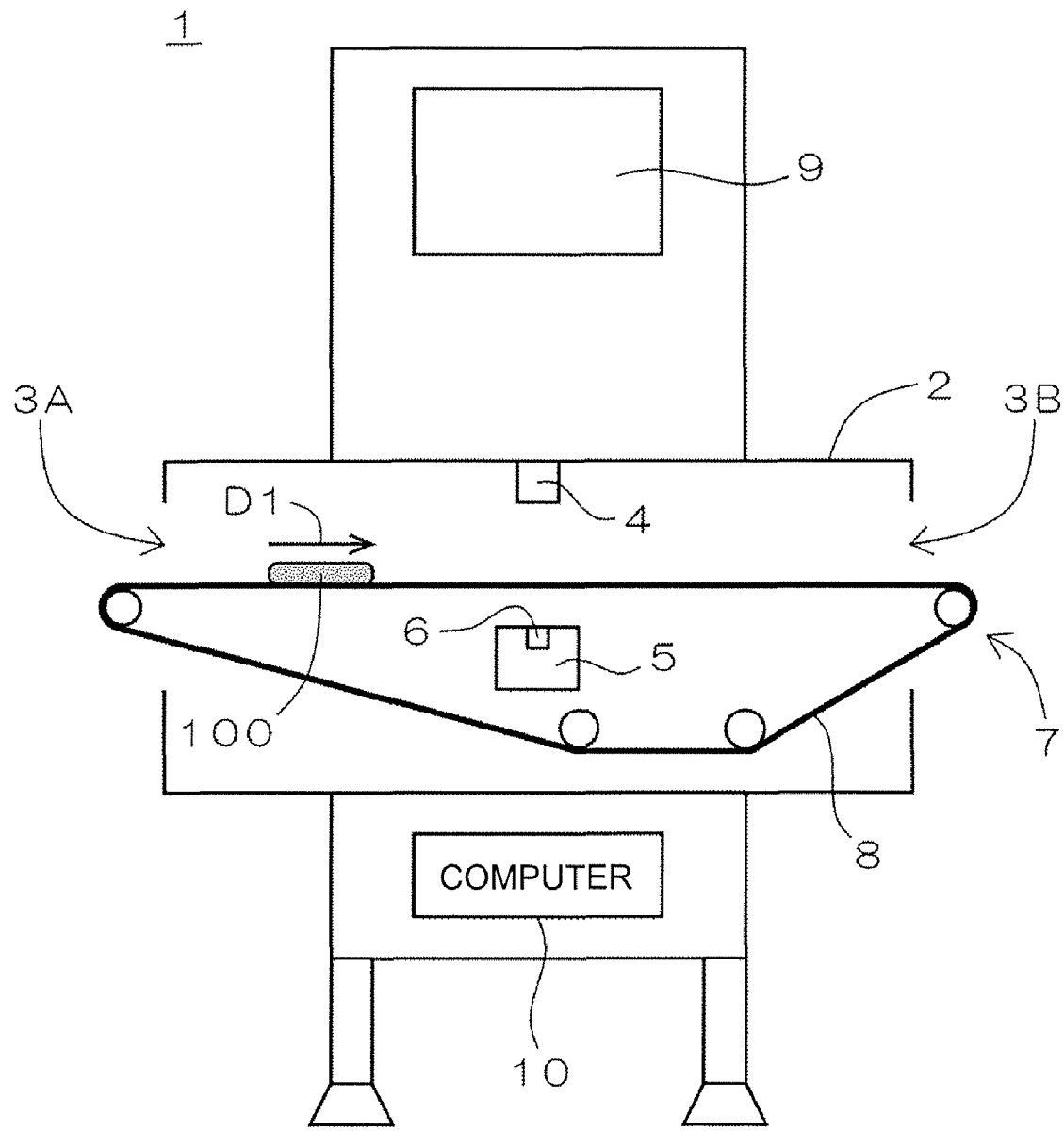
FIG. 1 is a schematic frontal view showing an example configuration of an X-ray inspection apparatus according to an embodiment of the present invention.

Embodiments of the present invention will now be explained in detail with reference to the drawings. Elements indicated with the same reference numerals in different drawings are either the same or corresponding elements.

FIG. 1 is a frontal view showing an example configuration of an X-ray inspection apparatus 1 according to an embodiment of the present invention.

A sealed box 2 is provided with an article inlet 3A and an article outlet 3B. The article inlet 3A is configured to convey an article 100 (e.g., a food product) into the sealed box 2 from the outside to be inspected. The article outlet 3B is configured to convey the article 100 out of the sealed box 2 after the article 100 has been inspected. FIG. 2 shows the structure of the apparatus with a front panel of the sealed box 2 removed in order to clearly illustrate the structure inside the sealed box 2.

An X-ray emitting section 4 and an X-ray detecting section 5 are arranged inside the sealed box 2. The X-ray detecting section 5 has a line sensor 6. The line sensor 6 extends along a direction perpendicular to the plane of the paper on which the figure is drawn. The X-ray emitting section 4 is arranged and configured to emit X-rays in a fan-like shape toward the line sensor 6. Thus, a space between the X-ray emitting section 4 and the line sensor 6 is designated as an X-ray emission path.

A carrying conveyor 7 is arranged inside the sealed box 2. The carrying conveyor 7 has a conveyor belt 8. The conveyor belt 8 is arranged across a plurality of rollers including a drive roller. The carrying conveyor 7 is arranged to carry an article 100 placed on an article carrying surface of the conveyor belt 8 such that the article 100 passes through the X-ray emission path established between the X-ray emitting section 4 and the line sensor 6. In the example shown in FIG. 1, the carrying conveyor 7 carries the article 100 in a direction indicated with an arrow D1. That is, the left-hand side of the figure is an upstream side and the right-hand side is a downstream side from the perspective of the article carrying direction.

The X-ray inspection apparatus 1 is equipped with a display section 9 having a touch panel function. A result of an inspection of an article 100 conducted by the X-ray inspection apparatus 1 is displayed on the display section 9. A computer 10 is installed inside the X-ray inspection apparatus 1. The computer 10 serve to process detection data acquired by the X-ray detecting section 5 and to control the operation of the X-ray inspection apparatus 1.

An article 100 targeted for inspection is supplied to an upstream end (left end in FIG. 1) of the conveyor belt 8 from an upstream side (left side in FIG. 1) of the X-ray inspection apparatus 1. Once placed on the conveyor belt 8, the article 100 is carried through the inside of the sealed box 2 from the upstream side to the downstream side such that it passes through the X-ray emission path. X-rays that have passed through the article 100 after being emitted from the X-ray emitting section 4 (transmitted X-rays) are detected by the line sensor 6 of the X-ray detecting section 5. If a contaminant exists inside the article 100, then the strength of transmitted X-rays detected by the line sensor 6 will extremely decrease at a position where the contaminant exists. As a result, the existence of contaminants inside the article 100, the sizes of the contaminants, and the locations of contaminants can be determined based on a strength distribution of transmitted X-rays detected by the line sensor 6.

FIG. 2 is a frontal view showing another example configuration of the X-ray inspection apparatus 1. This example is different from the example shown in FIG. 1 in that the computer 10 is externally connected to the X-ray inspection apparatus 1 with a signal cable instead of being installed inside the X-ray inspection apparatus 1.

FIG. 3 is a block diagram showing a configuration of the computer 10 shown in FIG. 1 or FIG. 2. The computer 10 includes a CPU 20, a memory 21 (computer readable medium) such as a RAM, and a storage device 22 such as a hard disk. It is acceptable for the storage device 22 to be an internal memory of the CPU 20. A prescribed program 23 is stored in the memory 21. The CPU 20 functions as a setting device 24, a determining device 25, a calculating device 26, and a display control device 27 by reading the program 23 from the memory 21 and executing the program 23. In other words, the program 23 is a program configured to make the computer 10 function as a storage device 22, a setting device 24, a determining device 25, a calculating device 26, and a display control device 27.

The operations of the X-ray inspection apparatus 1 according to this embodiment can be broadly separated into operations related to inspecting articles 100 using a threshold value that is currently set (hereinafter called "normal operations") and operations related to changing the set threshold value (hereinafter called "threshold value change operations").

During normal operations, the CPU 20 receives detection data SI related to the strengths of transmitted X-rays acquired by the X-ray detecting section 5. The determining device 25 determines if a contaminant exists inside an article 100 by comparing a strength of an X-ray expressed in the detection data S1 to a currently set threshold value (hereinafter called an "actual reference value"). The display control device 27 generates an image signal S2 for displaying an inspection result on the display section 9 and outputs the image signal S2.

The X-ray inspection apparatus 1 repeats the same inspection process with respect to each of a plurality of articles 100 that are continuously or intermittently supplied from an upstream apparatus. The storage device 22 stores detection data S1 acquired by the X-ray detecting section 5 regarding a plurality of articles 100 inspected within a prescribed immediately recent period (hereinafter called the "associated articles 100").

When changing the threshold value, a user performs an operation that causes the setting device 24 to set a desired hypothetical reference value. In this patent specification, the hypothetical reference value is a threshold value that is different from an actual reference value used during the actual inspections of the associated articles 100. In other words, the hypothetical reference value is a threshold value candidate to which the driver is considering changing the actual reference value and the hypothetical reference value will be set and used as the actual reference value if the user finalizes the change.

The determining device 25 compares the hypothetical reference value set by the setting device 24 to each of the detection data S1 stored in the storage device 22. Then, based on the comparison results, the determining device 25 determines if a contaminant would exist in each of the associated articles 100 assuming that the hypothetical reference value was used instead of the actual reference value.

The calculating device 26 calculates a contaminant existence rate (hereinafter called "hypothetical contaminant existence rate") based on the total number of associated articles 100 and the number of associated articles 100 that the determining device 25 determined that a contaminant is contained. In other words, the calculating device 26 calculates a hypothetical contaminant existence rate as a ratio of the number of articles 100 in which the determining device 25 has determined that a contaminant exists under the assumption that the hypothetical reference value was set with respect to the total number of associated articles 100.

The display control device 27 generates an image signal S2 and outputs the image signal S2. The image signal S2 is a signal for displaying an image including the hypothetical contaminant existence rate calculated by the calculating device 26 on the display section 9. An example of the image displayed on the display section 9 will be explained in detail later.

FIG. 4 shows an example of setting the threshold value. The horizontal axis of the graph shown in the figure indicates a position along a widthwise direction of the conveyor belt 8, and the vertical axis indicates a strength of an X-ray detected by the X-ray detecting section 5 after the X-ray has passed through an article 100. A strength distribution K1 of transmitted X-ray shows how the strengths of the X-rays passing through the article 100 decrease in accordance with the shape of the article 100. The strength distribution K1 has a downward peak P1 where the strength of transmitted X-rays is low due to the existence of a contaminant in a corresponding location of the article 100. The strength distribution K1 also has a peak P2 corresponding to signal noise.

The X-ray detecting section 5 obtains the smallest X-ray strength value of the strength distribution K1 as a detection datum S1. In the example shown in FIG. 4, the strength value at the tip of the peak P1 is obtained as the value of the detection datum S1 for that article 100.

The determining device 25 determines that a contaminant does not exist in the article 100 if the value of the detection datum S1 is equal to or larger than the threshold value and determines that a contaminant does exist in the article 100 if the value of the detection datum S1 is smaller than the threshold value.

Thus, if the threshold value is set to the value H1, then the value of the detection datum S1 (strength value at the tip of the peak P2) will be smaller than the threshold value H1 even if the peak P1 does not exist. In this case, signal noise will consequently be incorrectly detected as a contaminant.

If the threshold value is set to the value H3, then the value of the detection datum S1 (strength value at the tip of the peak P1) will be larger than the threshold value H3. In this case, an existing contaminant will consequently go undetected.

If the threshold value is set to the value H2, then the value of the detection datum S1 (strength value at the tip of the peak P1) will be smaller than the threshold value H2. Consequently, the contaminant can be detected correctly. Also, in this case, if the peak P1 did not exist, then the value of the detection datum S1 (strength value at the tip of the peak P2) would be larger than the threshold value H2 and the signal noise would not be mistakenly detected as a contaminant. Therefore, in the example shown in FIG. 4, the value H2 is the most appropriate threshold value.

In some situations, a food product manufacturer can allow a small quantity of contamination that will not harm a consumer (hereinafter called "allowable contamination") to exist. Thus, if a contaminant causing the peak P1 is an allowable contaminant, then it is preferable to set the threshold value to H3 from the perspective of reducing the failure rate (fraction defective) which is a ratio of the total number of inspected articles that are defective.

Figure 5:
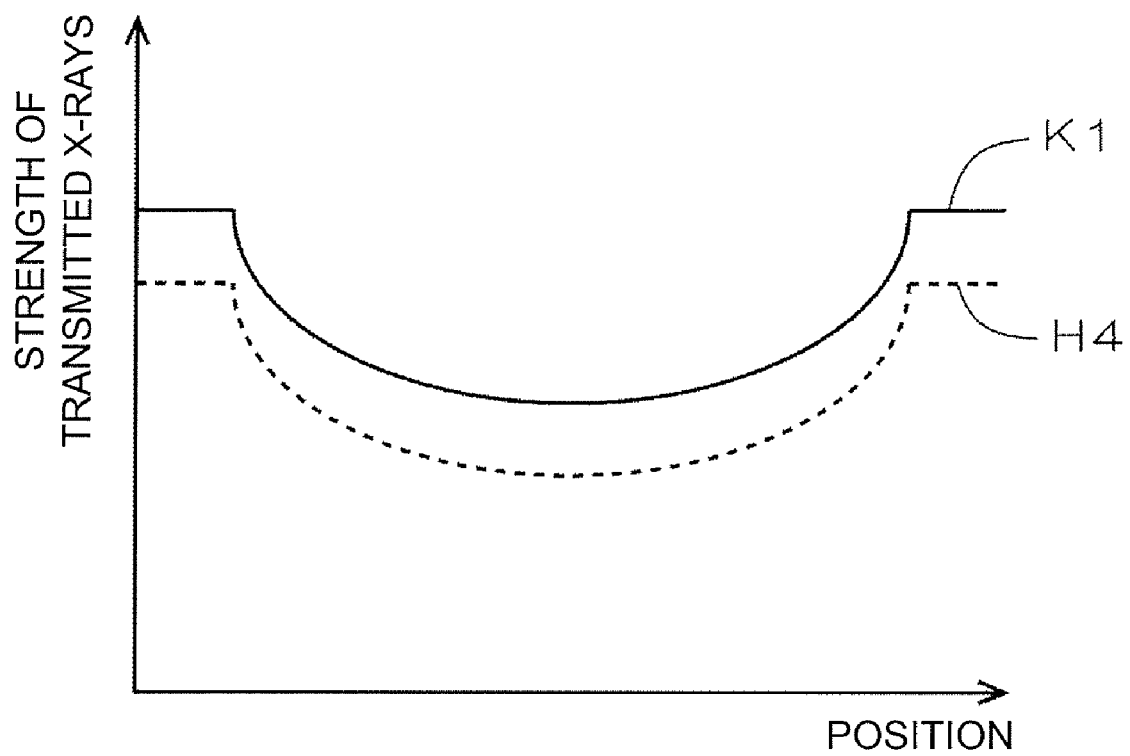
FIG. 5 shows another example of setting the threshold value.

FIG. 5 shows another example of setting the threshold value. Instead of the fixed threshold values H1 to H3 of the example shown in FIG. 4, it is also possible to set a threshold value H4 having a strength distribution corresponding to the strength distribution K1 of a non-defective article, as shown in FIG. 5.

Figure 6:
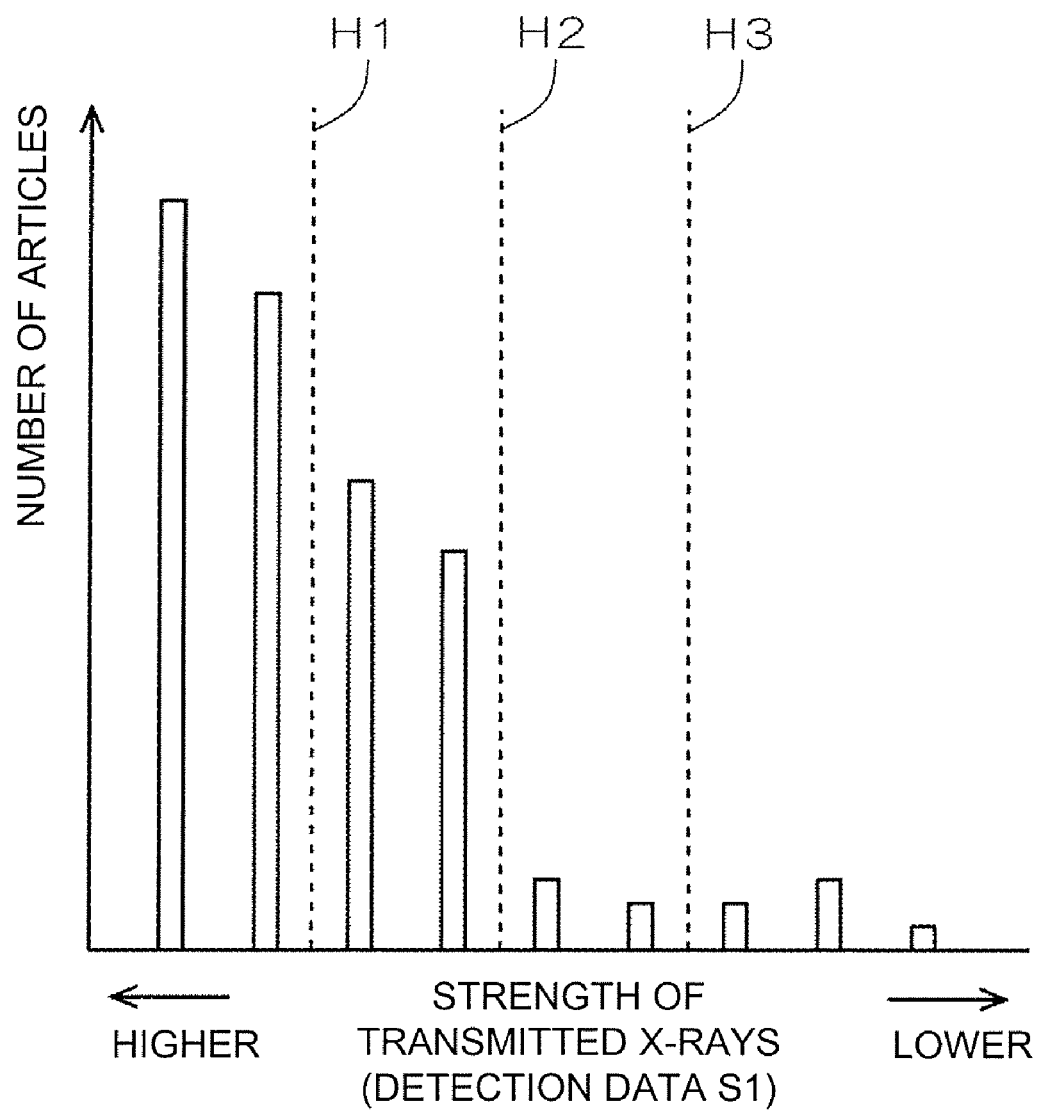
FIG. 6 is a graph illustrating a plurality of detection data stored in the storage section.

FIG. 6 is a graph illustrating a plurality of detection data S1 stored in the storage device 22. For example, if the threshold value is set to the value H2, all the articles 100 of which the strength of transmitted X-ray lies in the higher region than threshold value H2 (i.e., the region to the left of H2) are determined to be non-defective, and all the articles 100 of which the strength of transmitted X-ray lies in the lower region than threshold value H2 (i.e., the region to the right of H2) are determined to be defective.

Figure 7:
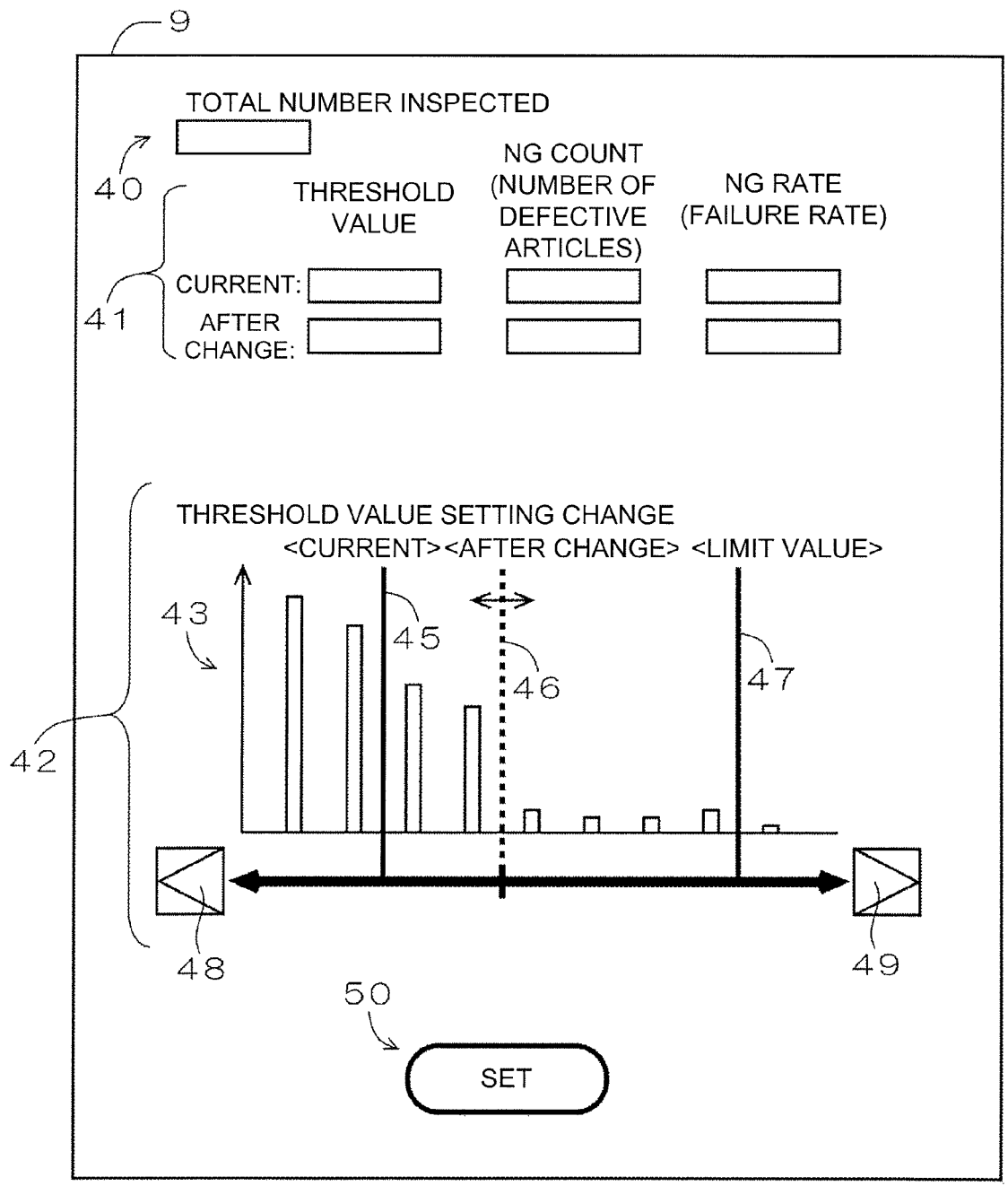
FIG. 7 shows an example of an image displayed on the display section during a threshold value change operation.

FIG. 7 shows an example of an image displayed on the display section 9 during a threshold value change operation. In a portion 40 of the image, the total number of associated articles 100 is displayed as the total number of inspected articles. More specifically, a total number of articles 100 inspected within a prescribed immediately recent period and of which detection data S1 have been stored in the storage device 22 is displayed.

In a portion 41 of the image, a currently set threshold value (actual reference value), a NG count (number of defective articles) and an NG rate (failure rate) corresponding to the actual reference value, a threshold value after change (hypothetical reference value), and a NG count (number of defective articles) and an NG rate (failure rate) corresponding to the hypothetical reference value are displayed. Information regarding current values and information regarding values that has changed are arranged above and below each other so that a worker can easily compare the values.

In a portion 42 of the image, a graphical FIG. 43 depicts the graph shown in FIG. 6 in a simpler form. In the graphical FIG. 43, a line 45 indicates the actual reference value and a line 46 indicates the hypothetical reference value. A direction indicating FIG. 48 indicating a leftward direction and a direction indicating FIG. 49 indicating a rightward direction are displayed diagonally below the graphical FIG. 43.

By touching the direction indicating FIG. 48, a worker can communicate with the CPU 20 such that the setting device 24 changes the hypothetical reference value to a higher value. By touching the direction indicating FIG. 49, a worker can communicate with the CPU 20 such that the setting device 24 changes the hypothetical reference value to a smaller value. The determining device 25 determines if each of the associated articles 100 contains a contaminant based on the changed hypothetical reference value. The calculating device 26 calculates a hypothetical contaminant existence rate (NG rate) based on the total number of associated articles 100 (total number of articles inspected) and the number of associated articles 100 that the determining device 25 determined that a contaminant is contained (NG count). The display control device 27 shifts the line 46 leftward or rightward within the graphical FIG. 43 and displays the changed threshold value, a corresponding NG count, and a corresponding NG rate in the portion 41.

In an X-ray inspection apparatus 1 according to this embodiment, a limit value (lower limit value) defining a range within which the hypothetical reference value can be set is set in advance in accordance with an allowable degree of contamination. The limit value is indicated by a line 47 displayed in the graphical FIG. 43. A worker can continue touching the direction indicating FIG. 49 until the line 46 overlaps the line 47, but, thereafter, the line 46 will not move any further to the right even if the worker touches the direction indicating FIG. 49. In this way, the hypothetical reference value is prevented from being set to a value smaller than the limit value.

Each time a worker touches the direction indicating FIG. 48 or 49, the line 46 moves within the graphical FIG. 43, and the changed threshold value, the NG count, and NG rate are updated in the portion 41. Therefore, the worker can, for example, search for a hypothetical reference value that can achieve a targeted failure rate, by referring to this information. Once the worker finds an appropriate hypothetical reference value, the worker touches a set button 50 displayed on the display section 9. As a result, the hypothetical reference value is used as the actual reference value in new inspections executed thereafter.

With an X-ray inspection apparatus 1 and program 23 according to this embodiment, the storage device 22 stores a plurality of detection data S1 related to the strengths of transmitted X-rays acquired by the X-ray detecting section 5 during inspections of the associated articles 100. During a threshold value change operation, the setting device 24 sets a hypothetical reference value that is different from an actual reference value used during the inspections of the associated articles 100. The determining device 25 compares the hypothetical reference value to the detection data S1 stored in the storage device 22 and determines if a contaminant exists in each article 100 based on the comparison results. The calculating device 26 calculates a hypothetical contaminant existence rate as a ratio of the number of articles 100 in which the determining device 25 has determined that a contaminant exists with respect to the total number of associated articles 100. Then, the display control device 27 displays the hypothetical contaminant existence rate on the display section 9.

Thus, when it becomes necessary to change an actual reference value setting, a hypothetical reference value as desired is set by using the setting device 24 and a hypothetical contaminant existence rate corresponding to the hypothetical reference value is displayed on the display section 9. As a result, the worker can use the hypothetical contaminant existence rate indicated on the display section 9 as an index so as to set the actual reference value more efficiently. Additionally, the hypothetical contaminant existence rate is not a prediction based on a simulation or the like but, instead, is calculated based on a plurality of detection data SI acquired during the actual inspection of the associated articles 100. Consequently, an accurate hypothetical contaminant existence rate can be provided to a worker.

With an X-ray inspection apparatus 1 according to this embodiment, a hypothetical contaminant existence rate can be calculated using detection data S1 acquired by the X-ray inspection apparatus 1 on an actual running manufacturing line (i.e., the detection data of the articles that have been inspected by the X-ray inspection apparatus on a production line that was actually running is stored). Thus, it is not necessary to stop the manufacturing line and execute a test run in order to find a hypothetical contaminant existence rate. As a result, the utilization rate of the manufacturing line can be increased.

With an X-ray inspection apparatus 1 according to this embodiment, both the actual contaminant existence rate (current NG rate shown in the portion 41 of FIG. 7) and the hypothetical contaminant existence rate are displayed on the display section 9. Consequently, by simply viewing the display section 9, a worker can easily compare the current actual contaminant existence rate to a hypothetical contaminant existence rate indicating after the reference value is changed. As a result, the task of changing the reference value setting can be accomplished more efficiently.

With an X-ray inspection apparatus 1 according to this embodiment, the display section 9 displays a limit value (the line 47 in the portion 42 of FIG. 7) within which the hypothetical reference value is allowed to be set. As a result, a worker can avoid, in advance, setting an unrealistic reference value that is outside of an allowed range and causing an inspection accuracy of the X-ray inspection apparatus 1 to decline sharply.

FIRST MODIFIED EXAMPLE

An X-ray inspection apparatus 1 according to a first modified example has a plurality of detection algorithms and can execute a contaminant detection processing using each of the detection algorithms.

FIG. 8 is a block diagram showing a configuration of a determining device 25 according to the first modified example. The determining device 25 has filters 50A to 50C, comparators 51A to 51C, and a determining section 52. For example, the filter 50A and the comparator 51A are configured to execute contaminant detection in accordance with a detection algorithm that is well suited for detecting contaminants having a size of 2 mm or smaller. The filter 50B and the comparator 51B are configured to execute contaminant detection in accordance with a detection algorithm that is well suited for detecting contaminants having a size of 2 to 4 mm. The filter 50C and the comparator 51C are configured to execute contaminant detection in accordance with a detection algorithm that is well suited for detecting contaminants having a size of 4 mm or larger.

An image signal related to an X-ray transmission image created based on transmitted X-rays detected by the X-ray detecting section 5 is fed to the filters 50A to 50C as detection data S1. Each of the filters 50A to 50C has a different filter coefficient tailored to the corresponding detection algorithm and is configured to execute a filter processing with respect to the image signal so as to obtain detection data S1A, S1B, or S1C, respectively, related to the filter-processed image signal. The detection data S1A is outputted to the comparator 51A, the detection data S1B is outputted to the comparator 51B, and the detection data S1C is outputted to the comparator 51C.

A threshold value HA is fed to the comparator 51A, a threshold value HB is fed to the comparator 51B, and a threshold value HC is fed to the comparator 51C. The threshold values HA to HC can be set separately for each of the detection algorithms. The comparator 51A compares the strength of transmitted X-rays expressed by the detection data S1A to the threshold value HA, the comparator 51B compares the strength of transmitted X-rays expressed by the detection data S1B to the threshold value HB, and the comparator 51C compares the strength of transmitted X-rays expressed by the detection data S1C to the threshold value HC to determine if a contaminant exists in each of the articles 100 based on the each of the respective detection algorithms. Data S3A to S3C related to the results of the determinations executed respectively by the comparators 51A to 51C are sent to the determining section 52.

The determining section 52 also receives data R related to determination rules. The determination rules can be set as desired depending on, for example, food product manufacturers. The determining section 52 determines if each article 100 is defective or not based on the data R and the data S3A to S3C received from the comparators 51A to 51C and outputs data S4 expressing the determination results.

For example, in the case where the determination rule that sets contaminants having a size of 2 mm or smaller as allowable contaminants, as long as the data S3B and S3C indicate that a contaminant does not exist in a particular article 100 being inspected, the determining section 52 will treat the article 100 as non-defective even if the data S3A indicates that a contaminant exists. Meanwhile, in the case where the determination rule that does not set any size of contaminant as an allowable contaminant, the determining section 52 will treat the article 100 as defective if any one of the data S3A to S3C indicates that a contaminant exists.

FIG. 9 shows an example of an image displayed on the display section 9 during a threshold value change operation. In this variation, the portion 41 includes portions 41A to 41C corresponding to each of the detection algorithms. In the portion 41, "Level 1" corresponds to the detection algorithm that is well suited for detecting contaminants having a size of 2 mm or smaller, "Level 2" corresponds to the detection algorithm that is well suited for detecting contaminants having a size of 2 to 4 mm, and "Level 3" corresponds to the detection algorithm that is well suited for detecting contaminants having a size of 4 mm or larger. The content of each of the portions 41A to 41C is the same as that of the portion 41 shown in FIG. 7.

In this variation, the portion 42 includes graphical FIGS. 43A to 43C corresponding to each of the detection algorithms. The content of each of the graphical FIGS. 43A to 43C is the same as that of the graphical FIG. 43 shown in FIG. 7. Set buttons 50A to 50C corresponding to each of the graphical FIGS. 43A to 43C, respectively, are also displayed.

Additionally, portions 55 and 56 are displayed between the portion 41 and the portion 42. The portion 55 displays the current number of defective articles determined based on the actual reference value and, there-below, the number of defective articles after changing the reference value determined based on the hypothetical reference value. The portion 56 displays the current failure rate calculated based on the actual reference value and, there-below, the failure rate that is calculated after changing the reference value determined based on the hypothetical reference value.

In the X-ray inspection apparatus 1 according to the first modified example, the setting device 24 can set the hypothetical reference value separately for each of the detection algorithms, the determining device 25 can determine if a contaminant exists separately in accordance with each of the detection algorithms, and the calculating device 26 can calculate a hypothetical contaminant existence rate separately in accordance with each of the detection algorithms. The display section 9 also displays both a hypothetical contaminant existence rate (NG rate) and a failure rate of the articles 100 for each of the detection algorithms.

The threshold value change operation will now be explained using Level 1 as a representative example. Since the operation is the same for Level 2 and Level 3, explanations thereof are omitted.

By touching the direction indicating FIG. 48A, a worker can communicate with the CPU 20 such that the setting section 24 changes the hypothetical reference value of Level 1 to a higher value. Conversely, by touching the direction indicating FIG. 49A, a worker can communicate with the CPU 20 such that the setting section 24 changes the hypothetical reference value of Level 1 to a lower value. The determining section 25 determines if each of the associated articles 100 contains a contaminant based on the changed hypothetical reference value of Level 1. The calculating section 26 calculates a hypothetical contaminant existence rate (NG rate) for Level 1 based on the total number of associated articles 100 (total number of articles inspected) and the number of associated articles 100 that the determining section 25 determined that a contaminant is contained (number of NG articles) in accordance with the Level 1 detection algorithm. The display control device 27 shifts the line 46A leftward or rightward within the graphical FIG. 43A and displays the changed threshold value of Level 1, a corresponding NG count, and a corresponding NG rate in the portion 41A.

Each time a worker touches the direction indicating FIG. 48A or 49A, the line 46A moves within the graphical FIG. 43A, and the changed threshold value of Level 1 and the values of NG count and NG rate calculated to occur after the change are updated in the portion 41A. The number of defective articles and the failure rate calculated to occur after the change are also updated in the portions 55 and 56. Therefore, the worker can search for a hypothetical reference value that can be used, for example, with the Level 1 detection algorithm to achieve a targeted failure rate by referring to this information. Once an appropriate hypothetical reference value has been found for Level 1, the worker touches the set button 50A.

As a result, the hypothetical reference value is used as the actual reference value of Level 1 in new inspections executed thereafter.

With an X-ray inspection apparatus 1 according to the first modified example, a worker can operate the setting device 24 to set a desired hypothetical reference value in accordance with each of the detection algorithms and the resulting hypothetical contaminant existence rate obtained for each of the detection algorithms is displayed on the display section 9. As a result, the worker can use the hypothetical contaminant existence rates indicated on the display section 9 for each of the detection algorithms as an index so as to set the actual reference value used in each of the detection algorithms more efficiently.

In an X-ray inspection apparatus 1 according to the first modified example, the display section 9 displays both the hypothetical contaminant existence rate and the failure rate of the articles calculated for each of the detection algorithms. As a result, a worker can visually check the information indicated on the display section 9 and search for a combination of hypothetical reference values that will achieve a targeted failure rate when set as the reference values used in the respective detection algorithms.

SECOND MODIFIED EXAMPLE

Figure 10:
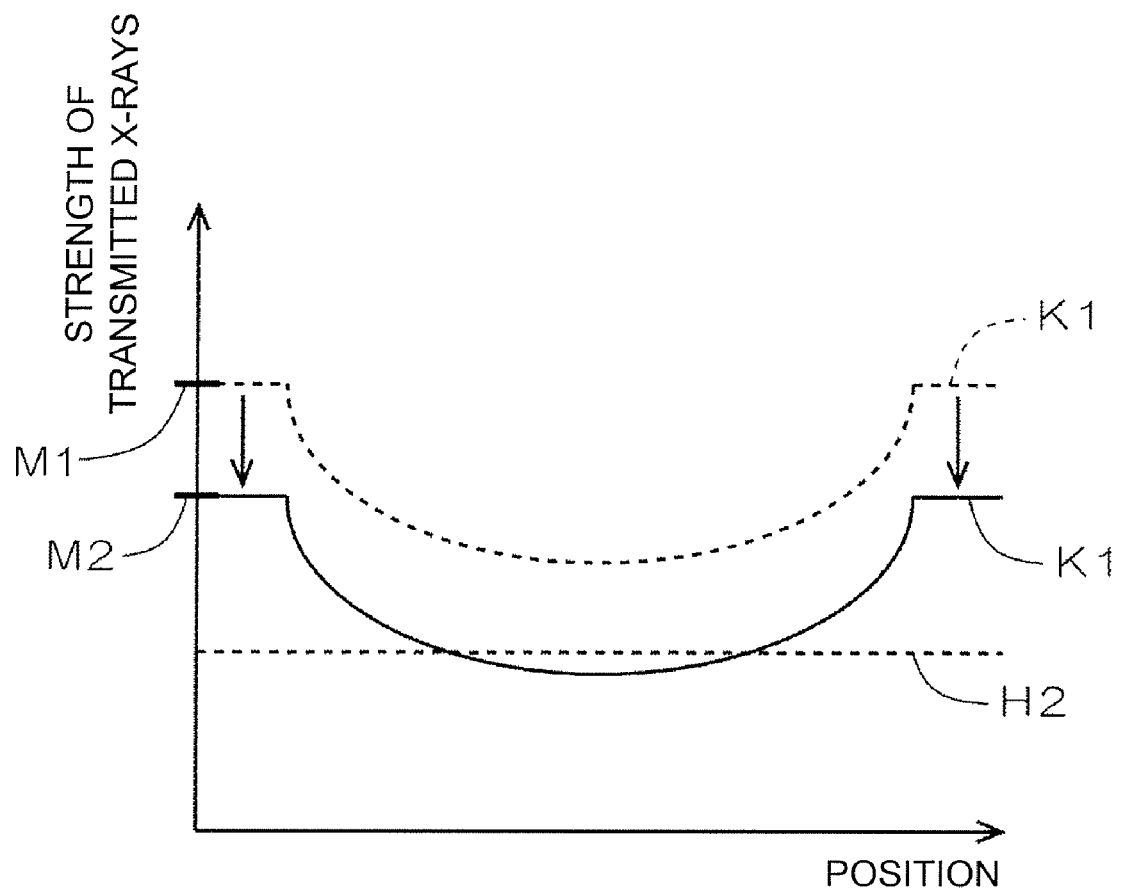
FIG. 10 illustrates a situation in which the strength of X-rays emitted from the X-ray emitting section has declined due to degradation over time.

FIG. 10 illustrates a situation in which the strength of X-rays emitted from the X-ray emitting section 4 has declined due to degradation over time. The strength distribution K1 indicated with a broken-line curve is a strength distribution based on X-rays emitted from the X-ray emitting section 4 when the X-ray emitting section 4 was in an initial state, and the strength distribution K1 indicated with a solid-line curve is a strength distribution based on X-rays emitted from the X-ray emitting section 4 after the X-ray emitting section 4 has degraded with the passage of time. As shown in FIG. 10, when the strengths of X-rays emitted from the X-ray emitting section 4 have declined due to degradation over time, the strengths of transmitted X-rays detected by the X-ray detection section 5 also decline across the entire strength distribution. As a result, a portion of the strength distribution K1 will be below the threshold value H2 and articles 100 will be incorrectly determined that a contaminant is contained even if they do not actually contain a contaminant.

In the second modified example, a strength of X-rays emitted from the X-ray emitting section 4 is detected and displayed on the display section 9 such that a worker can know when an X-ray source of the X-ray emitting section 4 is not operating properly or has degraded over time based on the information related to the X-ray strength indicated on the display section 9.

A strength of the X-rays emitted from the X-ray emitting section 4 can be ascertained, for example, by detecting a value of electrical current in a portion of the line sensor that is not overlapped by an article 100 and converting the value of electrical current into an X-ray strength value. As shown in FIG. 10, the strength of X-rays emitted from the X-ray emitting section 4 is detected as a strength value M1 when the X-ray emitting section 4 is in an initial state and as a strength value M2 after the X-ray emitting section 4 has become degraded due to the passage of time.

Figure 11:
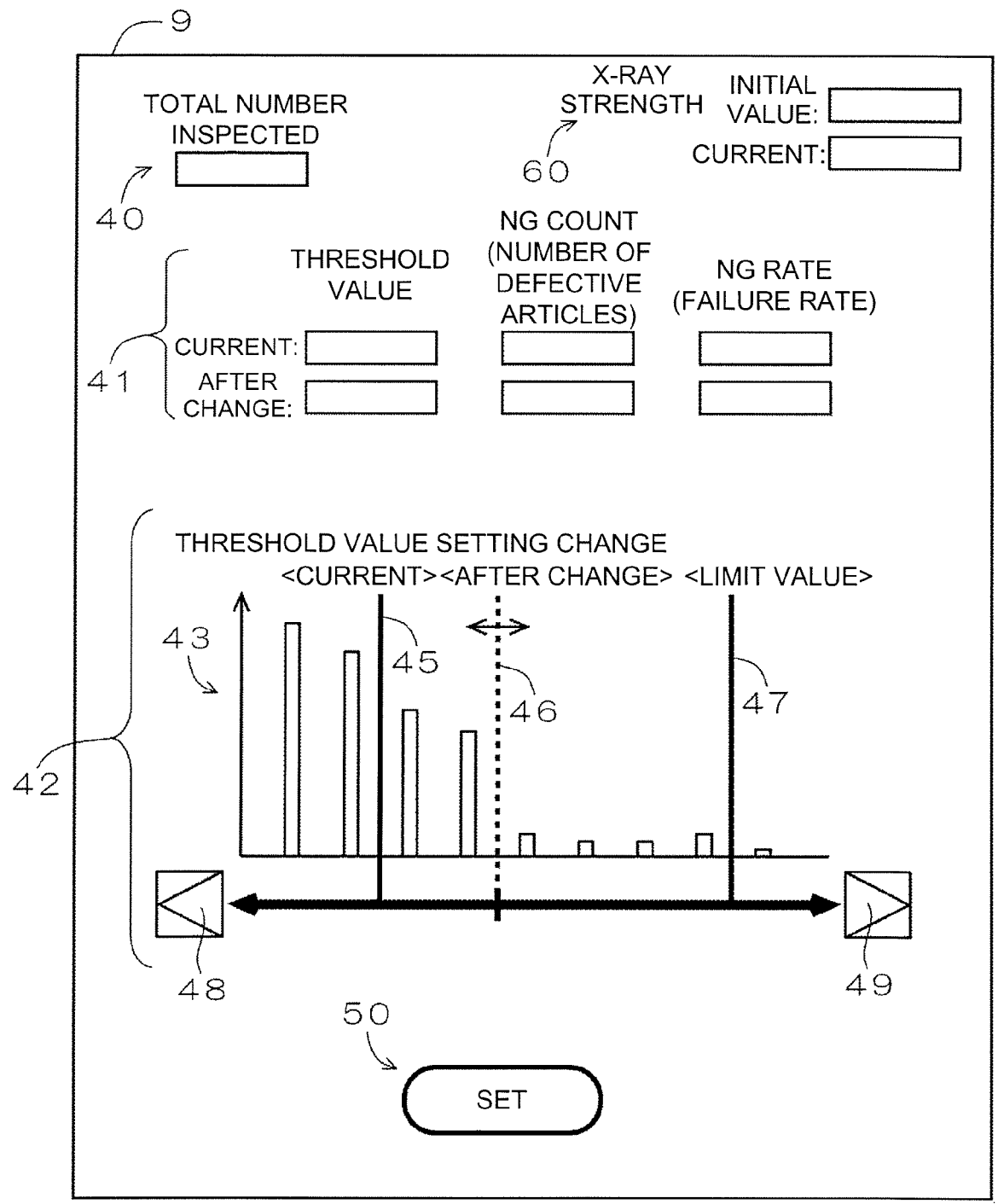
FIG. 11 corresponds to FIG. 7 and shows an example of an image displayed on the display section during a threshold value change operation according to a second modified example.
Figure 12:
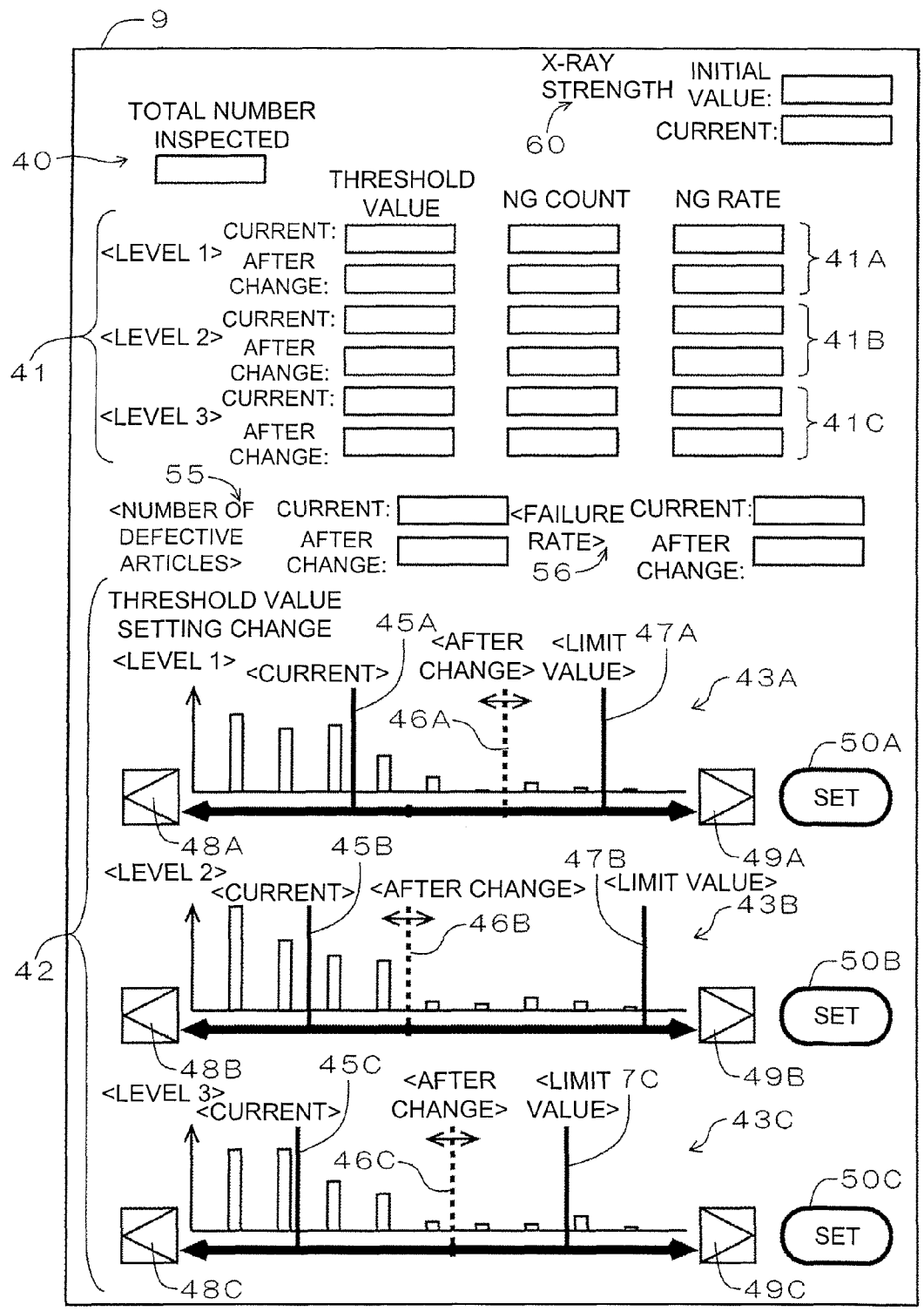
FIG. 12 corresponds to FIG. 9 and shows an example of an image displayed on the display section during a threshold value change operation according to the second modified example.

FIG. 11 corresponds to FIG. 7 and shows an example of an image displayed on the display section 9 during a threshold value change operation. FIG. 12 corresponds to FIG. 9 and shows an example of an image displayed on the display section 9 during a threshold value change operation. In this embodiment, a portion 60 is added to the display section 9. In the portion 60, an initial value and a current value of the strength of the X-rays emitted from the X-ray emitting section 4 are displayed above and below each other.

In an X-ray inspection apparatus 1 according to the second modified example, the display section 9 displays strength information regarding the X-rays emitted from the X-ray emitting section 4. Thus, a worker can know when an X-ray source of the X-ray emitting section 4 is experiencing trouble due to damage or degradation over time by referring to the information related to the strength of the X-ray indicated on the display section 9. As a result, the worker can avoid, in advance, needlessly changing a reference value without knowing that the X-ray source is not operating properly.

With the embodiments illustrated above, a reference value setting can be changed efficiently by providing a worker with an index for changing the reference value setting.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An X-ray inspection apparatus comprising:
   an X-ray emitting section that emits an X-ray beam at an article;
   an X-ray detecting section that detects the X-ray that has passed through the article and determines whether the article is defective based on a result of a comparison between a strength of the X-ray detected by the X-ray detecting section and a prescribed reference value;
   a storage device configured to store a plurality of detection data corresponding to strengths of the X-rays acquired by the X-ray detecting section during inspection of a plurality of articles;
   a setting device configured to set a hypothetical reference value that is different from the prescribed reference value used during the inspection of the plurality of articles;
   a determining device configured to determine whether a contaminant exists inside each of the plurality of articles based on a result of a comparison between the hypothetical reference value and each of the detection data stored in the storage device;

a calculating device configured to calculate a hypothetical contaminant existence rate as a ratio of a number of the plurality of articles in which the determining device has determined that a contaminant exists with respect to a total number of the plurality of articles; and a display control device configured to control a display section to indicate the hypothetical contaminant existence rate.

2. The X-ray inspection apparatus according to claim 1, wherein the storage device is configured to store the detection data of the plurality of articles that have been inspected by the X-ray inspection apparatus on an operating production line.

3. The X-ray inspection apparatus according to claim 1, wherein the display control device is further configured to control the display section to indicate the hypothetical contaminant existence rate calculated using the hypothetical reference value and the plurality of detection data, and an actual contaminant existence rate calculated using the prescribed reference value and the plurality of detection data.

4. The X-ray inspection apparatus according to claim 1, wherein the setting device is configured to set the hypothetical reference value separately for each of a plurality of detection algorithms for detecting a contaminant, the determining device is configured to determine whether a contaminant exists separately in accordance with each of the detection algorithms, the calculating device is configured to calculate the hypothetical contaminant existence rate separately in accordance with each of the detection algorithms, and the display control device is configured to control the display section to indicate the hypothetical contaminant existence rates calculated for all of the detection algorithms.

5. The X-ray inspection apparatus according to claim 4, wherein the determining device is further configured to determine whether an article is defective or not based on results of determinations of whether a contaminant exists made in accordance with each of the detection algorithms, and the display control device is configured to control the display section to indicate the hypothetical contaminant existence rate and a failure rate of the articles calculated in accordance with each of the detection algorithms.

6. The X-ray inspection apparatus according to claim 1, wherein the setting device is configured to accept the hypothetical reference value set on the display section, and the display control device is configured to control the display section to display a limit value within which setting of the hypothetical reference value is allowed.

7. The X-ray inspection apparatus according to claim 1, wherein the display control device is configured to control the display section to indicate a strength of an X-ray emitted from the X-ray emitting section.

8. A non-transitory computer readable medium embedded with a program executed by a computer that controls an X-ray inspection apparatus to emit an X-ray beam at an article from an X-ray emitting section, to detect an X-ray that has passed through the article with an X-ray detecting section, and to determine whether the article is defective based on a result of a comparison between a strength of the X-ray detected by the X-ray detecting section and a prescribed reference value, the program including instructions:

inspecting a plurality of articles using the X-ray detecting section;

storing detection data generated by the X-ray detecting section corresponding to the inspection of each of the plurality of articles;

retrieving the detection data;

setting a hypothetical reference value that is different from the prescribed reference value used during the inspection of the plurality of articles;

determining whether a contaminant exists inside each of the plurality of articles based on a result of a comparison between the hypothetical reference value and each of the detection data stored in the storage device;

calculating a hypothetical contaminant existence rate as a ratio of a number of the plurality of articles in which the determining device has determined that a contaminant exists with respect to a total number of the plurality of articles; and controlling a display section to indicate the hypothetical contaminant existence rate.

* * * * *